United States Patent [19]
Hailes et al.

[11] Patent Number: 5,571,685
[45] Date of Patent: Nov. 5, 1996

[54] MORPHINONE REDUCTASE FOR THE PREPARATION OF HYDROMORPHONE AND HYDROCODONE

[75] Inventors: Anne M. Hailes, Erith, United Kingdom; Christopher E. French, Palmerston North, New Zealand; Neil C. Bruce, Cambridge, United Kingdom

[73] Assignee: MacFarlan Smith Limited, Edinburgh, United Kingdom

[21] Appl. No.: 343,606

[22] PCT Filed: May 28, 1993

[86] PCT No.: PCT/GB93/01129

§ 371 Date: Nov. 30, 1994

§ 102(e) Date: Nov. 30, 1994

[87] PCT Pub. No.: WO94/00565

PCT Pub. Date: Jan. 6, 1994

[30] Foreign Application Priority Data

Jun. 25, 1992 [GB] United Kingdom ............... 9213524

[51] Int. Cl.⁶ .............................. C12Q 1/26; C12P 17/12
[52] U.S. Cl. .................................. 435/25; 435/4; 435/26; 435/122; 435/189
[58] Field of Search .................................... 435/4, 25, 26, 435/122, 148, 189, 190, 877; 436/816

[56] References Cited

U.S. PATENT DOCUMENTS 5,298,414  3/1994  Bruce ........................................ 435/26

5,387,515  2/1995  Bruce ........................................ 435/148

FOREIGN PATENT DOCUMENTS 2231332  11/1990  United Kingdom.
9013634  11/1990  WIPO.

OTHER PUBLICATIONS

Pollock S., Dihydromorphinone Retone Reductases UFE Sciences vol. 17 (1975) pp. 465–476.

Bruce N., Microbial Degradation of the Morphine Alkaloids, Arch Microbiol, (1990) 154:465–470.

"Microbial degradation of the morphine alkaloids. Purification and characterization of morphine dehydrogenase from *Pseudomonas putida* M10" (Bruce et al.), *The Biochemical Journal*, Mar. 15, 1991, vol. 274, No. 3, pp. 875–880.

*Primary Examiner*—Ralph J. Gitomer
*Attorney, Agent, or Firm*—Oliff & Berridge

[57] ABSTRACT

A morphinone reductase enzyme and related process provide for the preparation of hydromorphone from morphinone and hydrocodone from neopinone or codeinone. The enzyme has no significant activity with compounds of similar ring structure, has a molecular weight of approximately 81 kilodaltons and is composed of two identical subunits. The enzyme uses NADH as a cofactor and displays no significant enzymatic activity in the reverse direction.

9 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
       ( A ) LENGTH: 15 amino acids
       ( B ) TYPE: amino acid
       ( C ) STRANDEDNESS:
       ( D ) TOPOLOGY: linear ( i i ) MOLECULE TYPE: protein ( x i ) SEQUENCE DESCRIPTION: SEQ ID NO:1:

Pro Asp Thr Ser Phe Ser Asn Pro Gly Leu Phe Thr Pro Leu Gln
1               5                   10                  15

MORPHINONE REDUCTASE FOR THE PREPARATION OF HYDROMORPHONE AND HYDROCODONE

FIELD OF THE INVENTION

This invention relates to a new enzyme and to its use.

BACKGROUND OF THE INVENTION

Current synthesises of the analgesic hydromorphone (dihydromorphinone) and the antitussive hydrocodone (dihydrocodeinone) use uneconomic reagents, chemical catalysts and activating groups, and have undesirable effects on the environment. For example, hydromorphone is made by catalytic reduction of morphine with finely-divided platinum or palladium in acidic media. The product is purified by the addition of sulphur dioxide gas to saturation point. This mixture is left to crystallise over a period of 4–5 days, the complex is filtered, dried, and then decomposed by heating at 90° C. in concentrated hydrochloric acid until sulphur dioxide evolution ceases.

Biocatalysts can provide a cleaner technology. However, the range of enzyme activities presently available is rather limited, and these enzymes do not catalyse the reaction required.

GB-A-2231332 describes an acetylmorphine carboxylase that catalyses the hydrolysis of heroin, 3-acetylmorphine and 6-acetylmorphine to morphine, and also a morphine dehydrogenase that oxidises morphine to morphinone, utilising NADP as a cofactor. These enzymes are obtained from a novel strain of *Pseudornones putida* designated as "M10", NCIMB 40119. They can be used for the detection of heroin and morphine.

SUMMARY OF THE INVENTION

The present invention is based on the discovery of an enzyme which can be used as a biocatalyst in the synthesis of hydromorphone and hydrocodone. This is a highly specific NADH-dependent reductase that catalyses the reduction of the 7,8-unsaturated bond of morphinone and codeinone. The reaction of the enzyme, morphinone reductase, requires a cofactor such as reduced nicotinamide adenine dinucleotide (NADH) which is oxidised to NAD+ concurrently with the reduction of morphinone to hydromorphone.

DESCRIPTION OF THE INVENTION

The morphinone reductase of the invention can be defined in different several ways, but is probably best defined by its partial amino-acid sequence shown below, in the Sequence Listing.

Alternatively, or in addition, the morphinone reductase of the invention can be characterised by any of the following properties. With the aid of a cofactor, notably NADH, it reduces morphinone and codeinone to hydromorphone and hydrocodone, respectively. It also reduces neopinone to hydrocodone. It has no significant activity with other compounds of similar ring structure. Another distinguishing feature of the morphinone reductase is that it has a native molecular weight of 81,000 Dalton (as determined by elution from a gel filtration column calibrated with marker proteins). The enzyme is comprised of two identical subunits with a molecular weight of 41,100 Dalton (as determined by electrospray mass spectrometry). The optimal activity of the enzyme is exhibited at pH 7.5–8.0, with maximal activity in 50 mM phosphate buffer at pH 8.0.

Examples 1 to 3 below describe other features of the morphinone reductase, but it is expected that it will be possible to vary some of those by changing the conditions of growth of the microorganism which produces it or by recombinant DNA technology, which can be used to produce the enzyme. Accordingly, it is preferred not to rely on such characteristics in the most general definition of the enzyme. Any one or more of them can be considered (as the context permits) as alternative parameters for use in defining the enzyme, but they are best seen as one or more preferred characteristics, additional to one or more of those described above.

The novel enzyme converts morphinone and codeinone to hydromorphone and hydrocodone, respectively. Accordingly it is now possible to reduce the 7,8-unsaturated bond of morphinone, codeinone and neopinone, enzymically in the presence of morphinone reductase and a cofactor such as NADH. The enzyme can therefore be used in diagnostic assays for the detection and quantitation of morphinone and codeinone.

The enzyme of the invention can be produced by culturing the known M10 microorganism on a source of carbon and nitrogen. Any conventional sources can be used but it is preferred to grow *P. putida* M10 on a carbon source comprising morphine. The morphinone reductase is produced constitutively and, therefore, the *P. putida* M10 can be cultured on glucose to produce a highly active preparation of morphinone reductase. Cultivation of the organism is generally aerobic. Any usual temperature, e.g. within the 20°–40° C. range, preferably 25° to 35° C. can be used. To obtain the enzyme, the cells can be disrupted in any conventional way. Preferably a cell-free extract is made. The enzyme is then recovered from cells or extract.

Instead of the precise starting organism deposited, a mutant thereof, e.g. derived from gamma-ray irradiation or use of a chemical mutagen, induction by culture on another medium etc. or a transconjugant thereof with another bacterium or an artificially-produced variant can be used. The ability of any such organism to give the novel enzyme can be determined by the skilled man.

The enzyme or some modification thereof can also be made by recombinant technology using methods well recognised in that art. These may entail producing the enzyme in another host organism.

The enzyme of the present invention is useful primarily as an industrial biocatalyst in the synthesis of hydromorphone and hydrocodone. This may involve using purified preparations of the enzyme. Alternatively, the enzyme could be used in an appropriate blocked mutant of the organism.

The enzyme of the invention is also applicable to the detection and quantitation of morphinone and codeinone in biological fluids, especially in urine and blood. The detection may be conducted spectrophotometrically, in various ways. For example, the reduction of morphinone may be used to drive a redox reaction in which a change in UV absorption occurs. Thus, the cofactor itself can be used to detect the reaction by observing the oxidation of NADH to NAD+, particularly as a decrease in absorbance at 340 nm.

As indicated above, the morphinone reductase enzyme may be obtained from the same deposited bacterium as that disclosed in GB-A-2231332 as a source of acetylmorphine carboxylesterase and morphine dehydrogenase enzymes. Those enzymes are respectively capable of catalysing the hydrolysis of heroin, 3-acetylmorphine and 6-acetylmorphine to morphine, and the oxidation of morphine (to morphinone), codeine and ethylmorphine. The N-terminus of the second of these enzymes has been sequenced.

The combination of the two known enzymes, and of the morphinone reductase of the present invention, all isolated from the same organism, provides a pathway from, say, heroin to hydromorphone.

The gene for the novel enzyme, optionally together with genes for the enzymes described in GB-A-2231332, may be isolated and transformed into a suitable host, by conventional recombinant technology. The transformed microorganism may be used to prepare hydromorphone or hydrocodone from a variety of precursors. The novel enzyme, optionally together with one or both of the known enzymes, may be used to assay a specimen for the presence of, say, morphinone or an earlier substrate in the pathway.

The following Examples illustrate the invention. Example 1 refers in particular to the purification and characterisation of morphinone reductase, Example 2 to its utility in the generation of hydrocodone, and Example 3 to a coupled assay.

EXAMPLE 1

1. Organism

Pseudomonas putida (M10) was isolated from industrial waste liquors (Bruce et al, (1990). Arch. Microbiol. 154:465–470) which were enriched with morphine as the sole source of carbon and energy.

2. Growth conditions

Cultures of *Pseudomon putida* (M10) were grown in 2 l Erlenmeyer flasks containing 750 ml of sterile defined mineral medium consisting of $(NH_4)_2SO_4$ (0.5 g/l), $K_2HPO_4$ (2.0 g/l), $KH_2PO_4$ (0.2 g/l) and $MgSO_4$(0.05 g/l). Trace elements, as described by Barnett and Ingram (J. Appl. Bacteriol. (1955) 18:131–148) were filter-sterilised, using 0.2 μm Sartorius filters and added to the sterile medium (1 ml per litre). The growth medium was further supplemented with filter-sterilised 10 mM glucose, as the sole carbon source, unless otherwise stated. The cultures were incubated at 30° C. on a rotary shaker set at 180 rpm for 48 hrs. Thereafter, the cultures were harvested by centrifugation (9000 rpm for 15 min in a Sorval RC-5C centrifuge, using a GS3 rotor, at 4° C.). The pelleted cells were resuspended in 50 mM potassium phosphate buffer plus 1 mM dithiothreitol, pH 7.0, at a concentration of 0.5 g/ml. Cell-free extract, maintained at 4° C. by means of a crushed-ice bath, was prepared by sonicating the cell suspension for periods of 15 s in a Soniprep 150 MSE Ultrasonic Disintegrator (Fisons Instruments, FSA Ltd.) at an amplitude of 10 μm, for a total period of 3 min. The crude cell extract was centrifuged (20,000 rpm for 30 min, using a SS34 rotor, at 4° C.) to pellet unbroken cells and cell debris.

3. Chromatography.

All steps were carried out at 4° C., and 1 mM dithiothreitol (DTT) was included in all solutions. Morphinone reductase was purified by affinity chromatography. The adsorbent used was Mimetic Yellow 2 (Affinity Chromatography Ltd., Isle of Wight, U.K.). A final volume of 50 ml was packed into a 50 mm diameter column. A linear flow-rate of approximately 30 cm/hour was maintained. The column was first equilibrated with 2 empty column volumes (ecv) of 50 mM potassium phosphate buffer adjusted to pH 7 (Buffer A). Up to 50 ml (1 ecv) of cell extract was pumped onto the column. The column was rinsed with 2 ecv of Buffer A and then with 1 M NaCl in Buffer A until the absorbance at 280 nm of the eluate dropped almost to the baseline. Typically this required 10 ecv of this eluant. Bound morphinone reductase was then eluted using 2 ecv of 0.6 M NaCl +5 mM NADH in Buffer A. Typically, further rinsing with this eluant did not elute significantly more activity. The column was then rinsed with 2 ecv of 1 M NaCl, 2 ecv of 1 M NaOH and 2 ecv of distilled water and stored in 20% ethanol.

Active fractions of eluate were pooled and diafiltered with Buffer A to reduce the concentrations of NaCl1 and NADH approximately 1000-fold. Diafiltration was carried out using an Amicon 8050 Ultrafiltration Cell fitted with a Filtron Omega Series membrane of nominal cut-off 10,000 Daltons. The product was then concentrated to approximately 5 ml and stored frozen at −20° C. in suitably sized aliquots.

4. Enzyme assays

Enzyme activity was assayed by measuring the rate of oxidation of NADH. The reaction mixture used contained 0.3 mM NADH and 0.3 mM codeinone in Buffer A unless otherwise specified. Assays were carried out at 30° C. NADH oxidation was followed by monitoring the decrease in absorbance at 340 nm, using a Hewlett-Packard 8452A Diode Array Spectrophotometer. The rate of NADH oxidation in the absence of codeinone (background rate) was also measured and subtracted from the rate in the presence of codeinone. One unit of enzyme activity was defined as that amount of activity oxidising 1 mole of NADH per minute under these conditions.

Protein concentration was measured by the method of Bradford (Anal. Biochem. (1976) 72:248–254) using the Bio-Rad Protein Assay Reagent according to the protocol provided by Bio-Rad. Bovine Serum Albumin was used as a standard.

5. Electrophoresis.

SDS-Polyacrylamide Gel Electrophoresis (SDS-PAGE) was carried out using the Bio-Rad Mini-Protean II electrophoresis system. Acrylamide gels (12 % w/v) were cast and run according to the protocols supplied by Bio-Rad. Gels were typically run at 200 V for 45 minutes. Gels were stained using 0.1% Coomassie Brilliant Blue R-250 in 40% methanol, 10% acetic acid and destained in 2 changes of 40% methanol, 10 % acetic acid. Native (non-denaturing) PAGE was carrried out in the same way except that samples were not denatured, SDS was omitted from gels and gels were fixed with 20% trichloroacetic acid prior to staining.

6. Molecular weight determination.

The native molecular weight of morphinone reductase was determined by gel filtration chromatography according to the method of Andrews (Biochem. J. (1964) 91:222–233). A column of 16 mm diameter, 75 cm in length, packed with Sephacryl S-200 (Pharmacia) was used. The flow-rate was 8 ml/hour. Molecular weight standards used were bovine liver catalase, yeast C300 hexokinase, bovine serum albumin (BSA) and cytochrome C, with molecular weights of 240, 000, 100,000, 67,000 and 13,000 Daltons respectively. Catalase and hexokinase were detected by their activities according to the methods given in Bergmeyer ((1986) Methods of Enzymatic Analysis, 3rd edition, V.C.H. Publishers, Weinheim, Germany). BSA was detected by its absorbance at 280 nm an cytochrome C by its absorbance at 505 nm.

Subunit molecular weight was determined by SDS-PAGE using the Low Molecular Weight Standards of Bio-Rad, and also by electrospray mass spectrometry. Purified morphinone reductase was prepared for electrospray mass spectrometry by diafiltering with distilled water to reduce the concentrations of phosphate and DTT 1000-fold and then adding methanol to 50% v/v and acetic acid to 1% v/v. Mass spectrometry was performed using a VG Bio-Q Mass Spectrometer (VG Analytical Ltd., Manchester, U.K.).

7. Flavin assays.

Flavin was dissociated from morphinone reductase by boiling for 3 minutes and removal of denatured protein by ultrafiltration. Absorbance spectra of free and bound flavin were measured in quartz cuvettes using a Hewlett-Packard 8452A Diode Array Spectrophotometer. Thin layer chromatography (TLC) of flavins was performed on silica plates using solvent systems 2 and 4 of Fazekas and Kokai (Met. Enzymol. (1971) 18B:385–398), viz. 12:3:5 n-butanol:acetic acid:water and 2% disodium hydrogen phosphate in water. Flayins on TLC plates were visualised by their yellow fluorescence when illuminated by ultraviolet light at 366 nm. Luciferase assay of flavins was performed using the commercially-available preparation of *Vibrio harveyii* luciferase of Sigma. The reaction mixture contained 0.1 mg/ml luciferase preparation, 0.1 mg/ml bovine serum albumin, 0.2 mM n-decanal, 0.5 mM NADH and 1.5mM dithiothreitol. Assays were carried out at 24° C. and light emission was measured using a BioOrbit 1250 Luminometer (Labsystems (UK) Ltd., Basingstoke, U.K.). Deflavomorphinone reductase was prepared by ammonium sulphate treatment, as described by Husain and Massey (1978) Met. Enzymol. 53:429–437.

RESULTS

1. Purification.

Morphinone reductase was purified by affinity chromatography. Data from a representative purification are given in Table 1. The product appeared pure by SDS-PAGE. Specific activity of the product was generally 15 to 20 units per mg of protein.

TABLE 1

Purification of morphinone reductase
Starting Material: 10.2 g (wet weight) of *Pseudomonas putida* M10 cells.

|  | Cell Extract | Product |
| --- | --- | --- |
| Volume (ml) | 30.2 | 3.70 |
| Activity (U/ml) | 1.46 | 6.71 |
| Total Activity (U) | 44.1 | 24.8 |
| Yield |  | 56% |
| Protein (mg/ml) | 8.95 | 0.356 |
| Specific Activity (U/mg) | 0.163 | 18.8 |
| Purification factor |  | 115 |

2. Molecular weight determination.

Gel filtration with standard proteins of known molecular weight suggested a molecular weight for morphinone reductase of approximately 81,000 Daltons. SDS-PAGE gave a subunit molecular weight of around 44,000 Daltons. Electrospray mass spectrometry gave a subunit molecular weight of 41,120 Daltons with a standard error of 3 Daltons. It was therefore concluded that morphinone reductase in its native state exists as a dimer.

3. Prosthetic group.

The absorbance spectrum of purified morphinone reductase indicated that the enzyme was a flavoprotein. Upon boiling the enzyme and removal of denatured protein by ultrafiltration, the absorbance spectrum of the solution changed to that of a free flavin, indicating that the flavin is not covalently bound to the protein. The intensity of the flavin absorbance peaks gave a molar flavin concentration of twice the molar concentration of enzyme calculated from the protein concentration and molecular weight, suggesting that one molecule of flavin is bound per enzyme subunit. The liberated flavin comigrated with flavin mononucleotide (FMN) and not with flavin adenine dinucleotide (FAD) or riboflavin in two thin layer chromatography systems. The liberated flavin gave a positive result in the luciferase assay which is highly specific for FMN (Chappelle and Picciolo, Met. Enzymol (1971) 18B:381–385). Authentic FMN also gave a positive result but authentic FAD and riboflavin did not. It was therefore concluded that the prosthetic group is non-covalently-bound FMN. The flavin could be dissociated from morphinone reductase by ammonium sulphate treatment as described by Husain and Massey, supra. Deflavomorphinone reductase prepared in this way showed no absorbance in the visible region and was inactive. Following incubation with FMN (30 minutes at 4° C.) and removal of free FMN by ultrafiltration, the flavoprotein spectrum was restored and approximately 80% of the activity in the standard assay was regained. Incubation with FAD did not cause restoration of the flavoprotein spectrum or of enzyme activity. Incubation with mixtures of FMN and FAD resulted in no greater activity than did FMN alone. These results indicate that FMN is the only flavin prosthetic group present.

Since electrospray mass spectrometry would not be expected to show a non-covalently bound prosthetic group, it is concluded that native morphinone reductase consists of two protein subunits of approximately 41,100 Daltons and probably two molecules of FMN, of which the molecular weight is 466 Daltons, giving a native molecular weight of approximately. 83,100 Daltons.

In native (non-denaturing) PAGE, purified morphinone reductase typically showed, in addition to the strong, active band attributed to morphinone reductase, one or two faint bands of slightly lower $R_f$. The slowest-migrating of these was found to comigrate with deflavo-morphinone reductase prepared as described above. On titration of deflavo-morphinone reductase with FMN, this band was gradually replaced firstly by the second unidentified band and finally by the band corresponding to active morphinone reductase, although even with excess FMN, some of the former was always present. This suggests that the slower migrating of the faint bands observed in purified morphinone reductase represents deflavo-morphinone reductase. If active morphinone reductase contains 1 FMN group per subunit, then the second band may represent dimers from which one of these has been lost.

Both native-PAGE and isoelectric focusing of the purified enzyme gave one sharp band and one broad diffuse band, the relative intensities varying. Incubation of the sample with excess FMN prior to native-PAGE caused the sharp band to vanish and the diffuse band to increase in intensity. FAD did not have this effect. It was concluded that the sharp band represents apoenzyme and the diffuse band holoenzyme.

4. pH optimum.

The activity of morphinone reductase was measured in the following buffers: 50mM phosphate at pH 6.0, 6.5, 7.0, 7.5 and 8.0; 50 mM MOPS at pH 6.5, 7.0, 7.5 and 8.0; 50 mM Tris at pH 7.5, 8.0, 8.5 and 9.0; and 50 mM glycine at pH 9.0, 9.5, 10.0 and 10.5. The optimum activity was found to be at pH 7.5 to 8.0, with maximum activity in phosphate buffer at pH 8.0, in which the activity was approximately 20% higher than under the standard assay conditions.

5. Kinetics and specificity.

Enzyme activity was tested with a variety of substrates. No activity was observed when NADPH replaced NADH.

Activity was detected against codeinone and neopinone. Activity against morphinone was demonstrated in a coupled enzyme system as described in Example 2. No activity was observed against morphine, codeine or isocodeine, which possess a hydroxy-group rather than a keto-group at carbon 6. No activity in the reverse direction was observed against hydrocodone or hydromorphone, the normal reaction products. However, the reverse reaction is energetically unfavourable and a low rate could be masked by the background NADH oxidation activity of the enzyme. No reverse reaction was found with oxycodone, oxymorphone or dihydrocodeine. None of the alkaloids tested appeared to inhibit activity against codeinone when added to the standard assay system at 1 mM. No activity was observed against the steroids progesterone and cortisone, which possess an unsaturated ring with the double bond $\alpha,\beta$ to a keto-group as in morphinone. However, these steroids were found to inhibit greatly the reaction with codeinone when added at 0.3 mM to the standard assay mixture. Very slight activity was detected against the simple cyclic compound 2-cyclohexen-1-one. This compound also inhibited the reaction with codeinone when added to the standard reaction mixture at 1 mM although to a much lesser extent than the steroids.

Assays were carried out at a range of substrate concentrations and apparent $K_m$ and $V_{max}$ were determined for codeinone and neopinone at 0.3 mM NADH. The apparent $K_m$ for NADH was measured at 0.3 mM codeinone. These data are shown in Table 2.

TABLE 2

Kinetic data for morphinone reductase
Parameters for alkaloids were measured at 0.3 mM NADH, $K_m$ for NADH was measured at 0.3 Mm codeinone.

| Substrate | Apparent $K_m$ (mM) | Apparent $V_{max}$ (U/mg) | Apparent $k_{cat}$ ($s^{-1}$) | $k_{cat}/K_m$ ($s^{-1}mM^{-1}$) |
|---|---|---|---|---|
| Codeinone | 0.25 | 32.0 | 44.4 | 178 |
| Neopinone | 0.43 | 16.6 | 23.0 | 53.5 |
| NADH | 0.050 | | | |

6. Inhibition of activity.

Purified enzyme was incubated with the following possible inhibitors: copper sulphate, the thiol-blocking agent p-hydroxymercuribenzoate (pHMB), the thiol-reducing agent dithiothreitol (DTT) and the metal-complexing agents ethylenediaminetetraacetic acid (EDTA) and 8- hydroxyquinoline (8HQ). Incubation was in the standard assay mixture without codeinone or NADH, firstly for 30 min at room temperature and secondly for 16 hours at 4° C. The enzyme concentration was approximately 3.3 μg/ml, 1/100 that of the purified enzyme stock. The results are shown in Table 3. Copper sulphate and p-hydroxymercuribenzoate were highly inhibitory, suggesting that a reduced sulfhydryl group is important for activity.

TABLE 3

Inhibition tests
Activities are given as percentages of the activity of the controls at the shorter time, which was 16.6 U/mg.

| | 30 min 20°C. | 16 h 4°C. |
|---|---|---|
| Control | 100 | 97 |
| 1 mM DTT | 94 | 94 |
| 0.01 mM pHMB | 37 | 19 |

TABLE 3-continued

Inhibition tests
Activities are given as percentages of the activity of the controls at the shorter time, which was 16.6 U/mg.

| | 30 min 20°C. | 16 h 4°C. |
|---|---|---|
| 0.02 mM pHMB | 0 | |
| 0.01 Mm CuSO$_4$ | 0 | |
| 0.5 mM EDTA | 100 | 97 |
| 0.05 mM 8HQ | 94 | 91 |

7. N-terminal sequence.

Purified enzyme was electroblotted to polyvinyl difluoride membrane and the N-terminal sequence was determined. The sequence is given below as SEQ ID No.1.

Examples 2 and 3

In Examples 2 and 3, the resolution and identification of morphine, codeine and their possible metabolites was achieved using such methods as high performance liquid chromatography (HPLC), thin layer chromatography (TLC), proton nuclear magnetic resonance (IH-NMR) and mass spectrometry (MS).

Reverse-phase HPLC analysis was performed on a Waters component system (Millipore Waters U.K. Limited, Watford) consisting of a model 510 pump, a model 712 WISP autoinjector and a Waters 994 programmable photodiode array detector set to 235 nm and 280 nm, 0–1 V fsd. Separation of samples (50 μl) was achieved on a 5 μm C18 Spherisorb ODS column (4.6×250 mm) (Anachem limited, Luton) with an isocratic solvent system, delivered at a flow rate of 1 ml/min. The mobile phase consisted of filter-sterilised 15 mM KH$_2$PO$_4$ (adjusted to pH 3.5 with 1 M H$_3$PO$_4$) in 30% (v/v) HPLC grade acetonitrile (degassed for 40 min prior to use). Integrations were performed using Maxima 820 software and UV absorbance scans of resultant peaks were measured between 190 and 350 nm using the programmable photodiode array detector.

TLC was performed using 0.2 mm thick plastic plates precoated with Silica Gel (Kiesegel 60 F254, Merck) developed over a path of 6–8 cm in a TLC tank previously saturated with solvent 1 (chloroform: methanol 80:20 v/v). The plates were subsequently dried, examined under a UV lamp at 254 nm and sprayed with Ludy Tenger solution. Metabolites were purified by preparative thin layer chromatography on glass plates coated with Silica Gel (250 μm thickness; Whatman 60 A F$_{254}$).

$^1$H-NMR scans were recorded on a Bruker spectrophotometer, using trimethylsilane as an internal standard and deuterated chloroform as solvent.

MS (+FAB) was performed on a Kratos model MF890 mass spectrometer, using methanol/dichloromethane as solvent unless otherwise stated.

Morphinone reductase activity was determined as described in Example 1.

EXAMPLE 2

Reaction mixtures containing purified morphinone reductase or crude cell extract, 2 mM codeinone, 2 mM NADH and 50 mM Tris HCl buffer, pH 8.0, in a final volume of 10 or 50 ml were incubated at 30° C. on a rotary shaker set at 180 rpm. Samples (1 ml) were removed at regular intervals and the oxidation of NADH followed by spectrophotometric analysis at 340 nm. Samples were returned to the reaction vessel after analysis. Following completion of the reaction (100 min for a 50 ml reaction mixture using 500 μl purified morphinone reductase, 6 U/ml), the reaction mixture was adjusted to pH 8.7 by the addition of $NaHCO_3$ and 1 M NaOH, cooled at 4° C. and solvent-extracted with 3 equal vols. cooled chloroform. The organic phase was dried using a 0.4 nm molecular sieve and the solvent removed by rotary evaporation. The remaining residue was redissolved in a small volume of chloroform (1 ml) and subsequently resolved by TLC analysis on silica gel plates in solvent 1. Typically, two positive spots were observed when viewed under a UV lamp (254 nm) or when sprayed with Ludy Tenger solution, with $R_f$ values of 0.41 and 0.33. The former spot was based on unchanged codeinone as indicated by comparison with a control of the authentic standard. The latter spot ($R_f$ =0.33) was not observed when boiled cell extract was included in the reaction mixture or when NADH was omitted, suggesting that it was a product of the incubation.

A range of morphine alkaloids was subjected to TLC in solvent 1. Hydrocodone bitartrate was found to have the same $R_f$ value as the reaction product. The reaction product was purified by preparative TLC on a glass plate coated with silica gel, pre-run and developed in solvent 1. The product band was removed from the glass plate and eluted with 10 ml methanol. The silica phase was separated from the solvent by centrifugation at 3000 rpm for 5 min in an Auto Bench Centrifuge, Mark IV (Baird and Tatlock) and the solvent removed by rotary evaporation. The remaining oily residue was submitted for analysis by $^1$H-NMR, along with authentic hydrocodone, for comparison.

In the NMR spectra of authentic hydrocodone and the reaction product, the peaks for hydrocodone were assigned as follows: a pair of doublets centred at 6.64 δ and 6.57 δ occurred as a result of the aromatic AB system consisting of two protons positioned at C-1 and C-2, and a singlet at 4.7 δ occurs due to the proton at C-5. The absence of peaks at 6.6 δ and 6.12 δ in the spectrum of the reaction product implies that saturation of the 7,8-bond of codeinone has occurred. The spectrum of the authentic hydrocodone was identical with the reaction product.

Further identification of the reaction product was obtained by comparison of its mass spectra with that of authentic hydrocodone, dissolved in methanol, dichloromethane, acetonitrile and acetone. Fragmentation patterns were identical for the reaction product and the hydrocodone standard, with a molecular ion of 299.

EXAMPLE 3

The substrate for morphinone reductase was biologically produced by shaking incubation of a mixture containing 2mM morphine, 2mM NADP+, freeze-dried purified morphine dehydrogenase reconstituted in 1 ml 50 mM Bis Tris Propane buffer (BTP) (8 U/ml) and 50 mM BTP buffer pH 8.0, in a total volume of 50 ml. At regular intervals, 1 ml samples were removed and the reaction stopped by the addition of 2 μl glacial acetic acid (HPLC grade). The precipitated protein was subsequently pelleted at 13,000 rpm in an MSE microfuge. HPLC analysis of the supernatant (20 μl), diluted with 1.98 ml mobile phase showed the decrease in morphine concentration ($R_t$ =3.5 min) coincident with the production of morphinone ($R_t$ =3.9). The concentration of morphine was determined by comparison with a standard curve (110 mM) of authentic morphine HCl treated in the same way as experimental samples. After no further decrease in morphine concentration was apparent (70 min), 2 mM NADH and 500 μl purified morphinone reductase (3 U/ml) were added to the incubation mixture. Continued analysis of the supernatant revealed a significant decrease in peak height ($R_t$ =3.9) after the addition of morphinone reductase and the continued decrease in the amount of morphine ($R_t$ =3.5). The UV spectra obtained from the former peak ($R_T$ =3.9), following the addition of morphinone reductase, showed homology with the UV spectrum of authentic hydromorphone, whilst no homology was evident previous to the addition of the reductase. Furthermore, authentic hydromorphone was shown to have a retention time of 3.9 min, suggesting that the reaction product (hydromorphone) comigrates with morphinone under these HPLC conditions.

We claim:

1. A purified morphinone reductase enzyme having the N-terminal amino-acid sequence:

Pro Asp Thr Ser Phe Ser Asn Pro Gly Leu Phe Thr Pro Leu Gln (Seq ID NO:1).

2. An enzyme according to claim 1, obtainable from the strain *Pseudomonas putida*, NCIMB 40119.

3. A purified morphinone reductase enzyme wherein:

(1) with NADH as cofactor said enzyme reduces morphinone to hydromorphone;

(2) with said cofactor said enzyme reduces codeinone and neopinone but has essentially no enzymatic activity in reverse direction;

(3) said enzyme has a molecular weight of about 81,000, as determined by gel filtration; and (4) in phosphate buffer said enzyme exhibits maximal activity at pH about 8.0.

4. A process of producing an enzyme, said enzyme having morphinone reductase activity, said activity comprising a capacity for reducing morphinone to hydromorphone, said process comprising: culturing an enzyme obtainable from the strain Pseudomonas putida, NCIMB 40119 or a mutant or variant thereof capable of producing a morphinone reductase enzyme which, with a cofactor, reduces morphinone to hydromorphone, wherein the culturing is conducted on a source of carbon and nitrogen, at a temperature of 20° to 40° C., until the morphinone reductase is produced disrupting the cells; identifying a fraction having said morphinone reductase enzyme activity; and recovering said morphinone reductase enzyme having said morphinone reductase activity.

5. A method for producing hydromorphone or hydrocodone, which comprises reducing morphinone or codeinone, respectively, in the presence of said enzyme according to claim 1.

6. A method according to claim 5, in which the morphinone or codeinone is produced in situ from a precursor thereof, in the additional presence of one or more enzymes that convert the precursor to morphinone or codeinone.

7. A method according to claim 6, wherein the precursor is at least one compound selected from the group consisting of heroin, 3-acetylmorphine, 6-acetylmorphine, morphine, codeine and ethylmorphine.

8. A method according to claim 5 wherein the method comprises reducing morphinone to hydromorphone.

9. A method according to claim 5, wherein the method comprises reducing codeinone to hydrocodone.

* * * * *